United States Patent
Nair et al.

(10) Patent No.: US 6,665,066 B2
(45) Date of Patent: Dec. 16, 2003

(54) MACHINE VISION SYSTEM AND METHOD FOR ANALYZING ILLUMINATION LINES IN AN IMAGE TO DETERMINE CHARACTERISTICS OF AN OBJECT BEING INSPECTED

(75) Inventors: Dinesh Nair, Austin, TX (US); Kevin L. Schultz, Georgetown, TX (US)

(73) Assignee: National Instruments Corporation, Austin, TX (US)

( * ) Notice: Subject to any disclaimer, the term of this patent is extended or adjusted under 35 U.S.C. 154(b) by 187 days.

(21) Appl. No.: 09/844,754

(22) Filed: Apr. 27, 2001

(65) Prior Publication Data

US 2002/0159053 A1 Oct. 31, 2002

(51) Int. Cl.$^7$ .............................................. G01N 21/00
(52) U.S. Cl. .................. 356/237.2; 356/237.2
(58) Field of Search ................... 356/239.3, 239.5, 356/239.7, 239.8, 237.1, 237.2, 237.3, 602, 603, 604; 382/154

(56) References Cited

U.S. PATENT DOCUMENTS

| | | | |
|---|---|---|---|
| 4,392,120 A | * 7/1983 | Mita et al. | 356/237.5 |
| 4,645,348 A | * 2/1987 | Dewar et al. | 356/603 |
| 4,978,224 A | * 12/1990 | Kishimoto et al. | 356/394 |
| 5,003,166 A | * 3/1991 | Girod | 382/106 |
| 5,175,601 A | * 12/1992 | Fitts | 356/604 |
| 5,450,204 A | * 9/1995 | Shigeyama et al. | 356/604 |
| 5,563,702 A | * 10/1996 | Emery et al. | 356/239.3 |
| 5,652,658 A | * 7/1997 | Jackson et al. | 356/237.5 |
| 6,025,905 A | 2/2000 | Sussman | |
| 6,072,897 A | * 6/2000 | Greenberg et al. | 382/144 |
| 6,191,850 B1 | * 2/2001 | Chiang | 356/237.4 |
| 6,252,623 B1 | 6/2001 | Lu et al. | |
| 6,392,754 B1 | * 5/2002 | Pingel et al. | 356/603 |

* cited by examiner

Primary Examiner—Michael P. Stafira
Assistant Examiner—Juan D Valentin II
(74) Attorney, Agent, or Firm—Meyertons Hood Kivlin Kowert & Goetzel, P.C.; Jeffrey C. Hood

(57) ABSTRACT

A machine vision system and method for performing illumination line analysis on an image of an object to detect defects in the object. The method may comprise projecting a pattern of lines on a surface of the object, and then generating an image of the surface of the object. The analysis method tracks left and right edges of each of the illumination lines to determine width and curvature of each of the lines, preferably using a bi-directional edge detection technique applied to a path perpendicular to the current orientation of the line. Information regarding the left and right edges of the line may be used to determine local widths and local orientations of the line. This information may be used to determine if a thinning or blooming of the line occurs, or if a change in curvature of the line occurs, which may indicate a possible defect in the object.

37 Claims, 9 Drawing Sheets

+ points located on a laser line using current method
— line across which the edges of the line are looked for
▭ located points used to measure width → direction of the tangent at a point on the edge of the laser line

MACHINE VISION SYSTEM AND METHOD FOR ANALYZING ILLUMINATION LINES IN AN IMAGE TO DETERMINE CHARACTERISTICS OF AN OBJECT BEING INSPECTED

FIELD OF THE INVENTION

The present invention relates generally to the field of machine vision, and more particularly to machine vision inspection of the surface of an object using structured illumination.

DESCRIPTION OF THE RELATED ART

Machine vision systems are often used to inspect objects to determine characteristics, abnormalities or defects in the object. One method that has been used to analyze an object for defects may be referred to as "structured illumination". Structured illumination may comprise projecting a pattern on an object and then acquiring an image of the object. The resulting image of the object will include an illumination pattern corresponding to the projected pattern. The image may then be analyzed to determine desired features or characteristics of the object. The illumination pattern may make it easier for a machine vision system to visually detect or identify characteristics, abnormalities or defects in the object. The illumination pattern may make it easier for a machine vision system to visually detect or identify abnormalities or defects in the pattern.

However, current methods for analyzing images of an object that has been illuminated with a pattern have proved to be inadequate for accurately detecting defects or abnormalities in the object. Thus a system and method is desired which can analyze illumination lines in an image to detect characteristics, abnormalities or defects of an object displayed in the image.

SUMMARY OF THE INVENTION

The present invention comprises various embodiments of a system and method for performing line analysis on an image of an object to detect defects in the object. The line analysis performed herein may also be referred to as image analysis using "structured illumination".

The machine vision system or inspection system may comprise a computer coupled to a video source, such as a camera. The machine vision system may also comprise a light source that operates to project the desired pattern on a surface of the object being inspected. The computer includes a processor or CPU coupled to system memory (RAM). The computer may further include or be coupled to a video capture device or image acquisition device that receives the image from the camera. The video source produces an analog or digital video signal which comprises an image of the object, wherein the image includes a pattern, preferably a line pattern, comprised on the object produced by the pattern element and the light source. The image may be received by the image acquisition device and provided to the computer. The computer may store and execute a software program to analyze the image of the object to identify characteristics, abnormalities or defects in the object.

In one embodiment, as noted above, the method may comprise projecting a pattern of lines ("illumination lines") on a surface of the object, and then generating an image of the surface of the object. The image may include the pattern of lines projected on the surface of the object, wherein each line includes a left edge and right edge. A seed line, e.g., a line perpendicular to the pattern of parallel lines, or a prior training analysis, may be used to determine initial information regarding the pattern of lines, such as the number of lines, orientation of the lines, and initial points of each line. Certain of the information regarding the pattern of lines may also be input by the user.

The analysis method may then track or trace each of the lines to determine width and curvature of each of the lines. In one embodiment, for each respective line, the method may comprise determining at least one point along the respective line in the image. The analysis method may then trace or track the left and right edges of the line. For example, the method may repeatedly determine left and right edge points of the line in the image using a bi-directional edge detection technique applied to a path perpendicular to the current orientation of the line, thereby operating to trace the line in the image. Information regarding the left and right edges of the line may be used to determine local widths and local orientations of the line. If the method detects that two or more neighboring lines overlap, the method continues to track the respective line until the overlap no longer occurs, upon which the method may continue to track the respective line.

The width information may be used to determine if a thinning of the line occurs that exceeds a preset threshold, wherein a thinning of the line that exceeds the threshold indicates a possible defect in the object. The orientation information may also be used to determine if a change in curvature of the line occurs that exceeds a preset threshold, wherein a change in curvature of the line occurs that exceeds the threshold indicates a possible defect in the object. Therefore, the information produced by the line analysis may be used to detect characteristics, abnormalities or defects in the object being inspected.

BRIEF DESCRIPTION OF THE DRAWINGS

A better understanding of the present invention can be obtained when the following detailed description of the preferred embodiment is considered in conjunction with the following drawings, in which.

Figure 1:
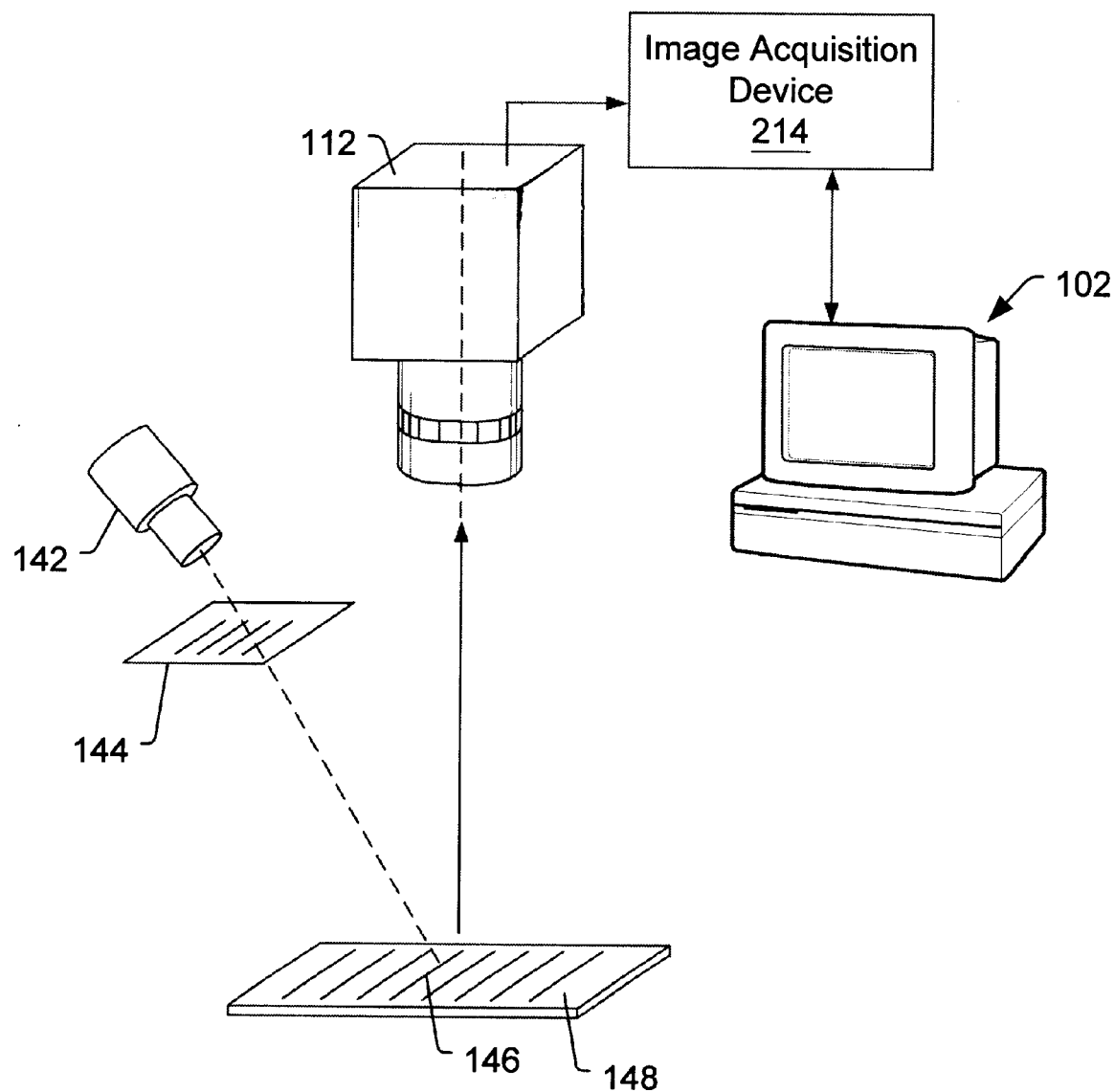
FIG. 1 illustrates an exemplary machine vision system or inspection system according to one embodiment of the invention.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE EMBODIMENTS

FIG. 1—Machine Vision System

FIG. 1 illustrates an exemplary machine vision system that may perform line analysis according to one embodiment of the invention. Stated another way, the machine vision system may perform analysis of an image using "structured illumination". The machine vision system may comprise a computer 102, an image acquisition device 214 comprised in or coupled to the computer 102, and a video source or camera 112 coupled to the image acquisition device 214.

The light source 142 may be any type of light source that generates a pattern of lines (also called "illumination lines" or "laser lines") on a surface of the object being inspected. As used herein, the terms "lines", "illumination lines" and "laser lines" are used interchangeably to refer to the lines projected onto the surface of an object, and which may be analyzed using the techniques described herein. As shown in FIG. 1, the machine vision system may comprise a light source 142 that generates light through a pattern element 144, thereby producing a desired pattern on a surface of the object being inspected. The pattern element 144 may be any of various types and may produce any of various types of patterns. The light source 142 may also or instead be a laser or other coherent light source. For example, the light source 142 may be a laser that scans the surface of the object, thereby projecting a pattern of illumination lines on the surface of the object. Thus, in one embodiment, the light source 142 is configured to generate the desired pattern, and a separate pattern element 144 is not required. The light source 142 may thus comprise any of various light sources.

Figure 8A:
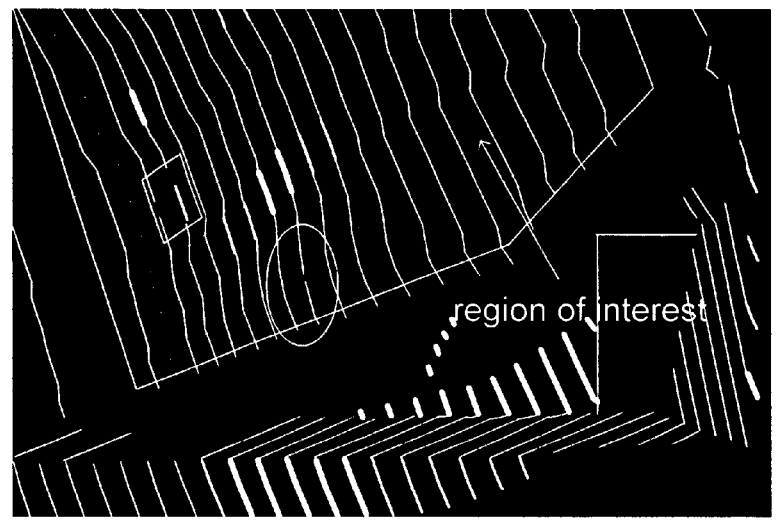
FIGS. 8A and 8B illustrate exemplary images which may be analyzed using methods of the present invention.
Figure 8B:
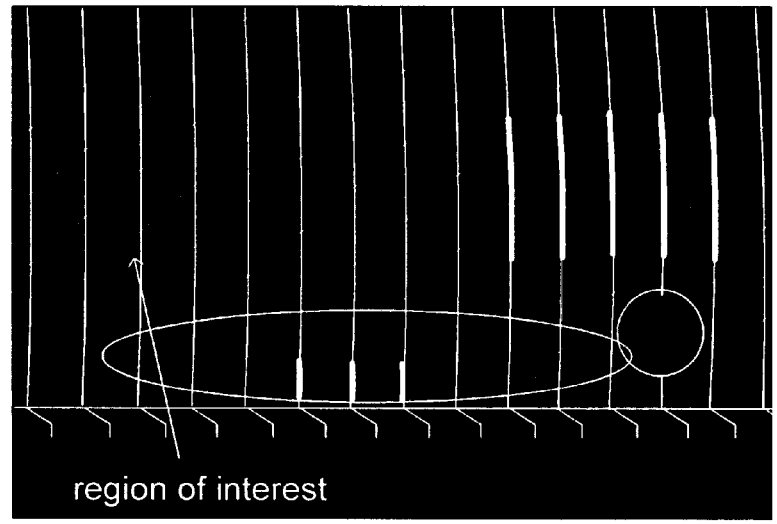

The light source 142 and/or pattern element 144 is designed to produce an array of illumination lines on the object being inspected, such as that shown in FIGS. 8A and 8B. The pattern element 144 may also be designed to produce a rectangular grid pattern such as that shown in FIG. 2 of U.S. Pat. No. 6,191,850, a circular grid pattern such as that shown in FIG. 3 of U.S. Pat. No. 6,191,850, or other type of pattern. In general, the light source 142 and/or pattern element 144 may produce any pattern that projects lines on the image, where the lines are preferably straight. In one embodiment, the light source 142 and/or pattern element 144 may produce lines on the image that are curved. Curved lines may be helpful in some applications in detecting defects. When a pattern of curved lines are projected, the curvature of the lines are preferably known by the software program in order to enable determination of abnormal changes in orientation.

The video source or camera 112 produces image data which comprises an image of the object 148. As shown, the image of the object includes a pattern of illumination lines 146 produced by the pattern element 144 and light source 142. The image data is provided to the computer 102 for processing. The computer 102 preferably executes a line analysis method according to one embodiment of the invention. For example, the computer 102 preferably includes a memory medium that stores a line analysis software program, wherein the software program is executed by a processor in the computer 102 to perform the line analysis.

The machine vision system may take any of various forms. As another example, the machine vision system may comprise an inspection system similar to that shown and described in U.S. Pat. No. 6,191,850, which is hereby incorporated by reference in its entirety as though fully and completely set forth herein.

Figure 2:
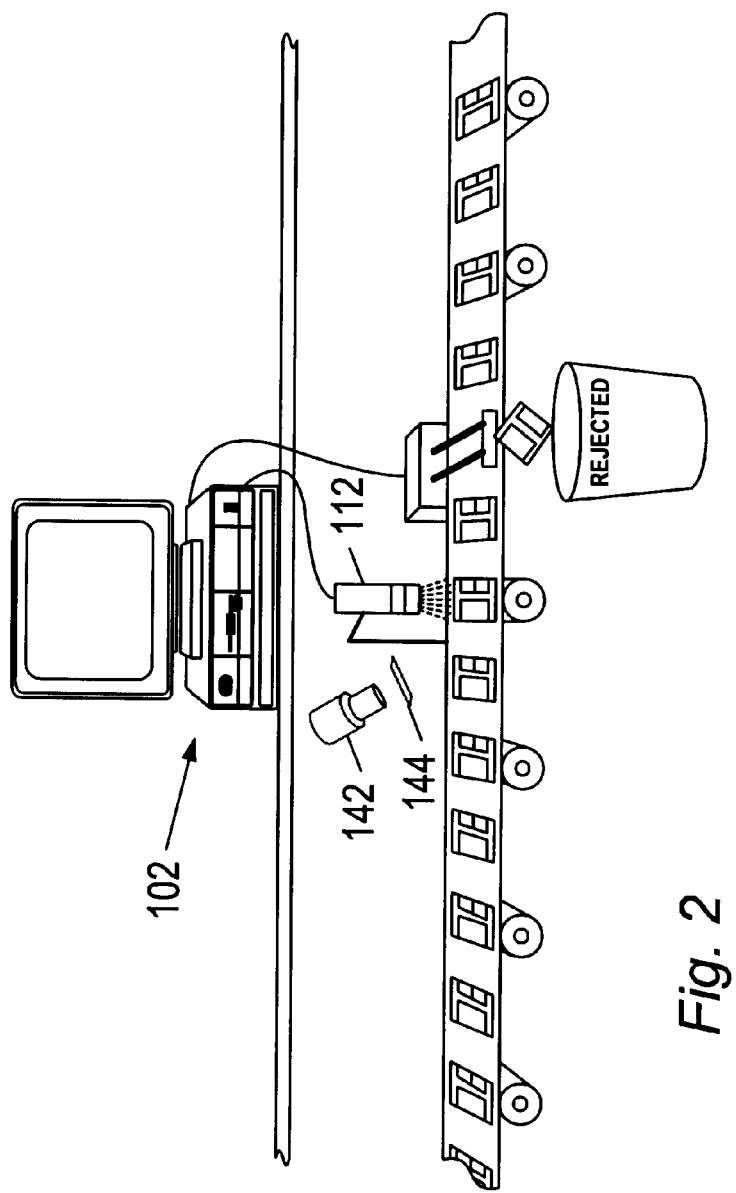
FIG. 2 illustrates an exemplary machine vision system used in inspecting objects.

FIG. 2—Exemplary Machine Vision Inspection System

FIG. 2 illustrates an exemplary machine vision system used in inspecting objects on an assembly line according to one embodiment of the invention. As described above, the machine vision system may comprise computer 102, image acquisition device 214 (not shown in FIG. 2) comprised in or coupled to the computer 102, and video source or camera 112 coupled to the image acquisition device 214. The machine vision system may also comprise light source 142 and optionally pattern element 144 which operate to produce a desired pattern on an object being inspected. As noted above, the light source may be a laser that operates to generate the desired pattern on the surface of the object being inspected, without the user of pattern element 144.

The objects on the assembly line may be any of various types of objects that require inspection. As one example, the objects being inspected may comprise floppy disks, as shown. As another example, the objects being inspected may comprise automobile parts, e.g., automobile body members. In an automotive application, the method may operate to analyze automobile body members to detect cracks dents or other abnormalities in the body member being inspected.

Figure 3:
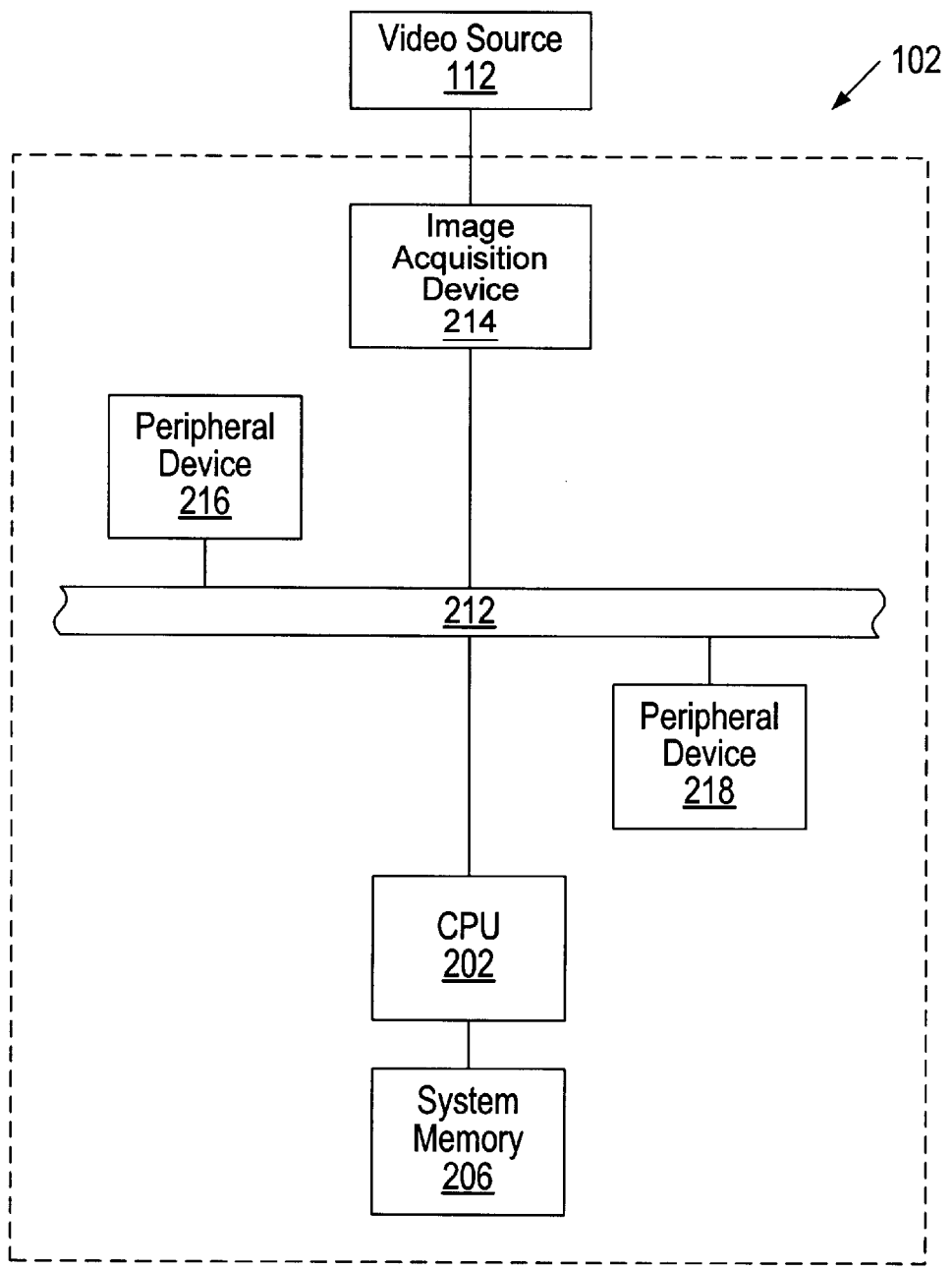
FIG. 3 is a high-level block diagram of the computer system according to one embodiment.

FIG. 3—Computer System Block Diagram

FIG. 3 is a high-level block diagram of the computer system 102 according to one embodiment. It is noted that the block diagram of FIG. 3 is exemplary only, and other computer system architectures may be used as desired. The computer 102 may comprise a processor or CPU 202, a system memory 206, and a peripheral bus 212. The CPU 202 is coupled to the system memory 206, optionally through a bridge or memory controller (not shown). The CPU 202 and the system memory 206 may couple to the peripheral bus 212. In the currently preferred embodiment, the peripheral bus 212 is the PCI expansion bus. However, other types of buses may be used. The system memory 206 may store a line analysis program according to one embodiment of the invention.

The computer system 102 also may include an image acquisition device 214, also referred to as a video capture device or board or frame grabber board, which is adapted for coupling to the video source 112. The image acquisition device 214 may be coupled to the peripheral bus 212. One example of image acquisition device 214 is described in U.S. Pat. No. 6,012,109, which is hereby incorporated by reference as though fully and completely set forth herein. In addition to the image acquisition device 214, other peripheral devices (216 and 218) may be coupled to the peripheral bus 212, as desired. For example, the peripheral device 216 may be a motion control board that controls operation or movement of the light source 142, the pattern element 144, and/or the location of the object.

The video source 112 supplies the image data to the image acquisition device 214. It is noted that the video source 112 may supply analog image data or digital image data to the image acquisition device 214. Where the image acquisition device receives an analog signal, the image acquisition device 214 may digitize the analog video signal to produce digital image data. The image acquisition device 214 may temporarily store the digitized image data until it can arrange for transfer to the system memory 206 through peripheral bus 212. When the image data is received in the system memory 206, the CPU 202 may execute the line analysis software program to analyze the image data. Operation of the line analysis method is described in greater detail below. In another embodiment, image acquisition device 214 may include an on-board processor, such as CPU and memory, or an FPGA, that operates to analyze the image data using the line analysis techniques described herein.

FIGS. 4, 5, 6 and 7 are flowchart diagrams illustrating operation of the line analysis method according to one embodiment of the invention. It is noted that each of FIGS. 4, 5, 6 and 7 illustrate one embodiment, and other embodiments of the method may be used as desired. For example, various steps in the flowcharts may be performed in a different order than that shown, or omitted, or various other steps may be added to the method, as desired.

Figure 4:
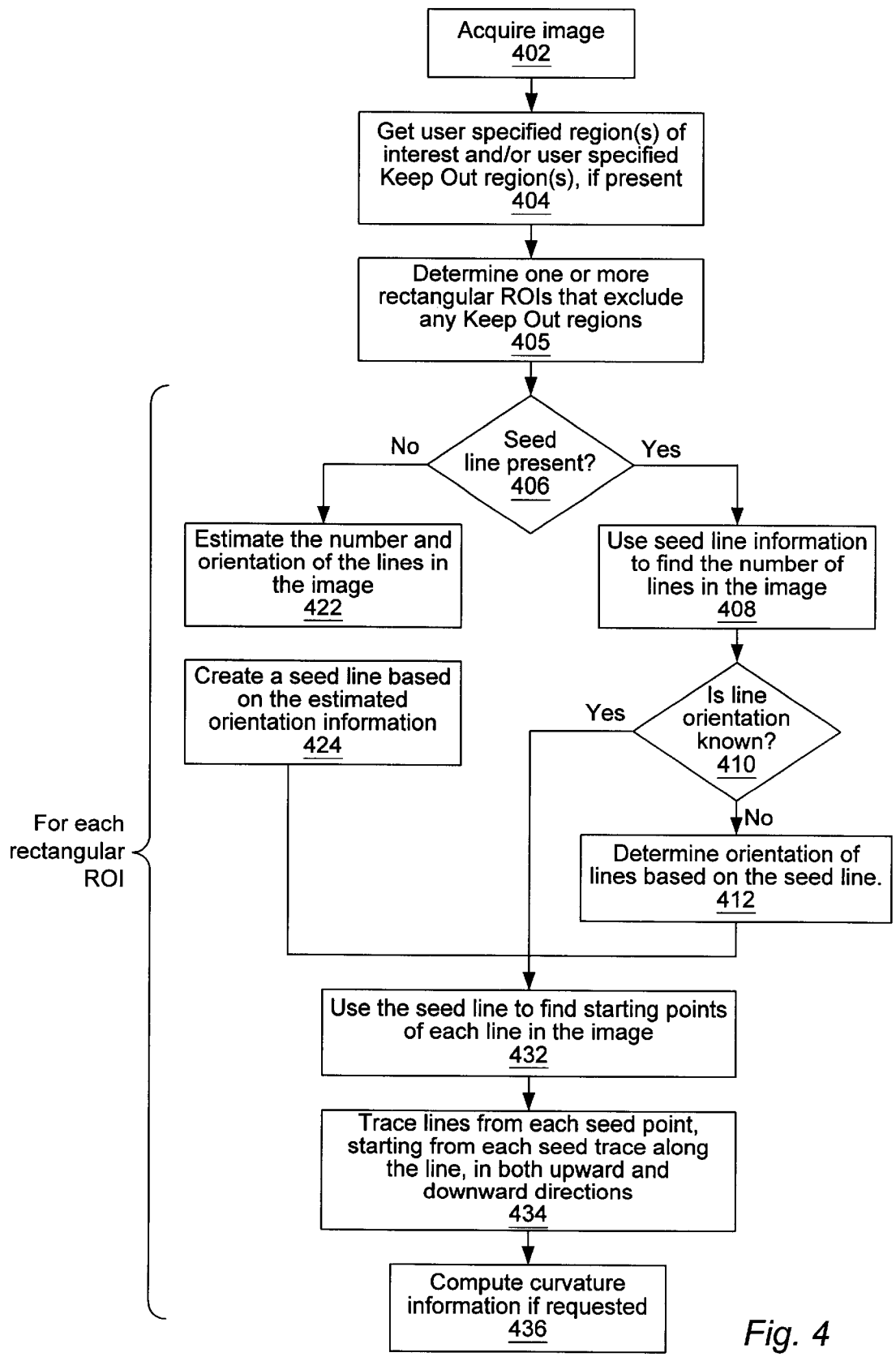
FIG. 4 is a flowchart diagram illustrating operation of the illumination line analysis method according to one embodiment of the invention.

FIG. 4—Line Analysis Method

FIG. 4 is a flowchart diagram illustrating operation of the line analysis method according to one embodiment of the invention. The method described in FIG. 4 may operate to detect and trace illumination lines in an image. One objective of the method is to trace the illumination lines in order to detect abnormalities such as cracks, thinning, bends and/or folds along each illumination line. These abnormalities may correspond to deformations or defects in the part or object being inspected.

The method described in FIG. 4 may also be used as part of a training step to train the method on a sample object or part to pre-compute information regarding illumination lines contained in the image. For example, the training step may operate to pre-compute the coordinates of a particular edge, e.g., the left edge, of each illumination line in the image. This may save processing during later inspections. The training step may also operate to pre-compute the orientation of the illumination lines, the number of illumination lines, and/or other information that can save processing during later inspections.

As shown, in step 402 the image is acquired. The image may comprise a plurality of pixels. The image may be black and white, gray scale, or a color image. As discussed above, the image comprises an image of the object with a pattern superimposed on a surface of the object in the image, such as shown in FIGS. 8A and 8B. The pattern is preferably an array of parallel illumination lines, or illumination lines that are substantially parallel. The pattern may also comprise two arrays of parallel illumination lines, e.g., a grid. The pattern may also comprise different configurations of lines, as discussed above. The array of parallel lines is useful in analyzing the image for defects. The image may be acquired from the camera 112, or the image may have been previously acquired and may be obtained from a memory medium.

In step 404 the method may obtain the user specified region of interest, if present. Thus, if the user has specified a region of interest, this region of interest (ROI) of the image is used in subsequent processing. Portions of the image not contained in the ROI may be ignored. In step 404 the user may also specify one or more "Keep Out" or "Don't Care" regions in the image or ROI in which no image analysis is to be performed.

In step 405 the method may compute one or more regions of interest (ROIs) that exclude any "Keep Out" regions specified by the user. Thus, if the user specified a "Keep Out" region, then in step 405 the software program may automatically determine one or more ROIs, preferably rectangular ROIs, that, when combined, cover the portion of the image desired to be analyzed while excluding the "Keep Out" region. For example, in the image shown in FIG. 8B, a plurality of different rectangular regions may be formed that collectively cover the image but yet exclude the circular "Keep Out" region. In the following discussion, the image analysis steps described below in steps 506–536 are presumed to occur for each of the one or more ROIs that are created in step 405. Thus each of the created ROIs may be independently and separately processed per the flowchart steps described below. In one embodiment, each created ROI may have its own seed line to allow this independent processing.

In step 406 the method may determine if a seed line is present in the image. A seed line may be a line that is included in the pattern superimposed on the object that is perpendicular (or at a known orientation) to the array of lines (the "illumination lines" or "laser lines") comprising the pattern. Where a seed line may be present, the seed line is useful in determining the orientation of the array of lines comprising the pattern as well as the number of lines in the pattern. Thus in step 406 the method, i.e., the software program, may have been pre-programmed with knowledge of the location of the seed line. The seed line may be pre-specified by the user or may be discovered through a prior training phase. Thus, the location of the seed line may be input by the user or may be determined in a prior training phase. In either case, the exact or approximate pixel location of the seed line may be pre-stored in the software program. In one embodiment, in step 406 the method searches for the seed line using edge detection techniques.

As noted above, the seed line may be useful in determining the expected number and orientation of lines in the image. An alternate method is to process a training image (or region) that contains all of the illumination lines without any defects, wherein this information may be obtained from analysis of the training image.

If a seed line is determined to be present in the image in step 406, then in step 408 the method may use the seed line information to find the number of illumination lines in the image. Since the seed line is known to be perpendicular to the array of lines comprising the pattern, the method can perform an edge detection along the seed line and count the number of parallel lines contained in the pattern. Alternatively, the number of parallel lines contained in the pattern may be input by the user or may be determined in a prior training phase.

In step 410 the method may determine if the orientation of the array of parallel lines is known. If so, then operation proceeds to step 432. If the orientation of the array of parallel lines is determined to not be known in step 410, then in step 412 the method may determine the orientation of the lines based on the seed line. The orientation of the parallel lines or illumination lines is assumed to be perpendicular to the orientation of the seed line. Thus, the method may use the known location and orientation of the seed line to determine the orientation of the array of parallel lines. This computation may simply involve computing an orientation 90 degrees from the seed line orientation. After step 412, operation proceeds to step 432.

If a seed line is determined to not be present in the image in step 406, then in step 422 the method may estimate the number of illumination lines and the orientation of the illumination lines in the image. This estimation is performed without use of a seed line in the image, since no seed line is present in the image. This estimation performed in step 422 is described in greater detail with respect to the flowchart of FIG. 5. It is noted that, if the orientation of the lines is known a priori, e.g. from a prior training step or from user input, the overhead associated with computing the orientation of the lines may be advantageously avoided.

After the method estimates the number of illumination lines and the orientation of the illumination lines in the image in step 422, in step 424 the method may create a seed line based on the estimated orientation information. In other words, in step 424 the method may create the coordinates of a "virtual" seed line that is perpendicular to the array of parallel lines (illumination lines) in the image. Operation then proceeds to step 432.

In step 432 the method may use the virtual seed line to find starting points of each illumination line in the image. Thus in step 432 the method may traverse the image along or parallel to the virtual seed line and perform an edge detection to determine the starting points of each illumination line in the image.

In step 434 the method may trace illumination lines from each seed intersection point, starting from each seed trace along the illumination line in both upward and downward directions. In other words, in step 434 the method may, for each respective illumination line, and beginning at the intersection of the seed line and the respective illumination line, trace the illumination line in one of an upward or downward direction, followed by tracing the illumination line in the other direction. The trace operation may comprise determining edge points or edge pixels (or sub-pixels) of the line for each of the left edge and right edge of the line.

During the trace operation, the method may determine the local width of the illumination line at each pixel increment, or at certain pixel increments, of the illumination line and may also determine local orientations of the illumination line. This trace operation is used in determining or identifying defects in the object being inspected. The method may apply a local filtering operation during the trace operation to remove noise. This trace operation performed in step 434 is described in greater detail with respect to the flowchart of FIG. 6.

In step 436 the method may, if requested, compute curvature information of each respective illumination line. The curvature information may be computed from the local orientations computed in step 434. This curvature information may also be used in determining or identifying defects in the object being inspected.

Figure 5:
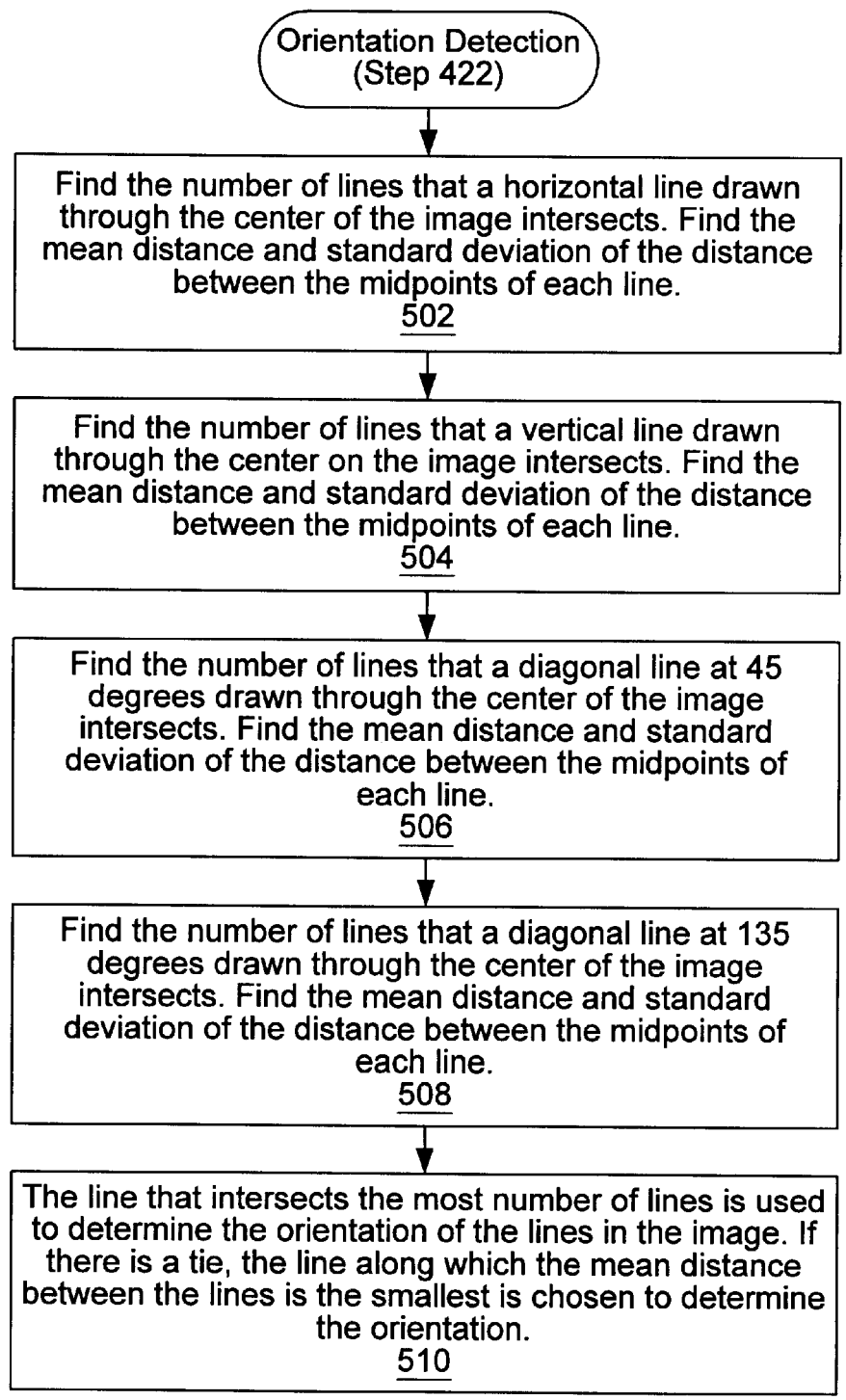
FIG. 5 is a flowchart diagram of a method for detecting orientation of the lines in the image performed in step 422 of FIG. 4.

FIG. 5—Illumination Line Orientation Detection Method

FIG. 5 is a flowchart diagram illustrating operation of step 422 of FIG. 4 according to one embodiment, which comprises estimating the number of illumination lines and the orientation of the illumination lines in the image (without the use of a seed line from the image).

As shown, in step 502 the method may determine the number of illumination lines that intersect a horizontal line drawn through the center of the image. This may be performed by computing the coordinates of an imaginary horizontal line in the image, and then finding edges along the coordinates of this imaginary horizontal line. An edge point where the pixel transition is from black to white is assumed to be beginning of a illumination line, and the next transition (from white to black) edge is assumed to be the end of the illumination line. In step 502 the method may also determine the mean distance and standard deviation of the distance between the midpoints of each illumination line.

In step 504 the method may determine the number of illumination lines that intersect a vertical line drawn through the center of the image. This may be performed by computing the coordinates of an imaginary vertical line in the image, and then finding edges along this imaginary vertical line. An edge point where the pixel transition is from black to white is assumed to be beginning of a illumination line and the next transition (from white to black) edge is assumed to be the end of the illumination line. In step 504 the method may also determine the mean distance and standard deviation of the distance between the midpoints of each illumination line.

In step 506 the method may determine the number of illumination lines that intersect a diagonal line at 45 degrees drawn through the center of the image. This may be performed by computing the coordinates of this imaginary diagonal line in the image, and then finding edges along this imaginary diagonal line. As before, an edge point where the pixel transition is from black to white is assumed to be beginning of a illumination line and the next transition (from white to black) edge is assumed to be the end of the illumination line. In step 506 the method may also determine the mean distance and standard deviation of the distance between the midpoints of each illumination line.

In step 508 the method may determine the number of illumination lines that intersect a diagonal line at 135 degrees drawn through the center of the image. This may be performed by computing the coordinates of this imaginary diagonal line in the image, and then finding edges along this imaginary diagonal line. As before, an edge point where the pixel transition is from black to white is assumed to be beginning of a illumination line and the next transition (from white to black) edge is assumed to be the end of the illumination line. In step 508 the method may also determine the mean distance and standard deviation of the distance between the midpoints of each illumination line.

In step 510 the method may determine the line that intersects the most number of illumination lines. The line that intersects the most number of illumination lines may be used to determine the orientation of the illumination lines in the image. If there is a tie, e.g., if two lines intersect approximately the same number of illumination lines, then the line along which the mean distance between the illumination lines is the smallest may be chosen to determine the orientation. For example, if the horizontal line intersects or "cuts" the most number of illumination lines, then the illumination lines in the image are deemed vertical. If two or more lines intersect or "cut" approximately the same number of illumination lines, then the mean distance between these two lines may be used to determine the orientation.

If two lines are determined to intersect the greatest number of illumination lines, but one line intersects a greater number of lines than the other, then a distance between these two lines that corresponds to or is proportionate to the relative number of lines that each intersects may be used as the orientation. In other words, the computed orientation line will be closer to the line that intersects the greater number of lines and farther from the line that intersects the lesser number of lines.

It is noted that the above method in step 510 may proceed in one or more additional iterations to more precisely determine the orientation of the line that intersects the most number of illumination lines. For example, the method may determine the two lines that intersect the greatest number of illumination lines, compute a line between these two lines, determine the number of illumination lines intersected, and so on, until a desired precision is obtained.

Figure 6:
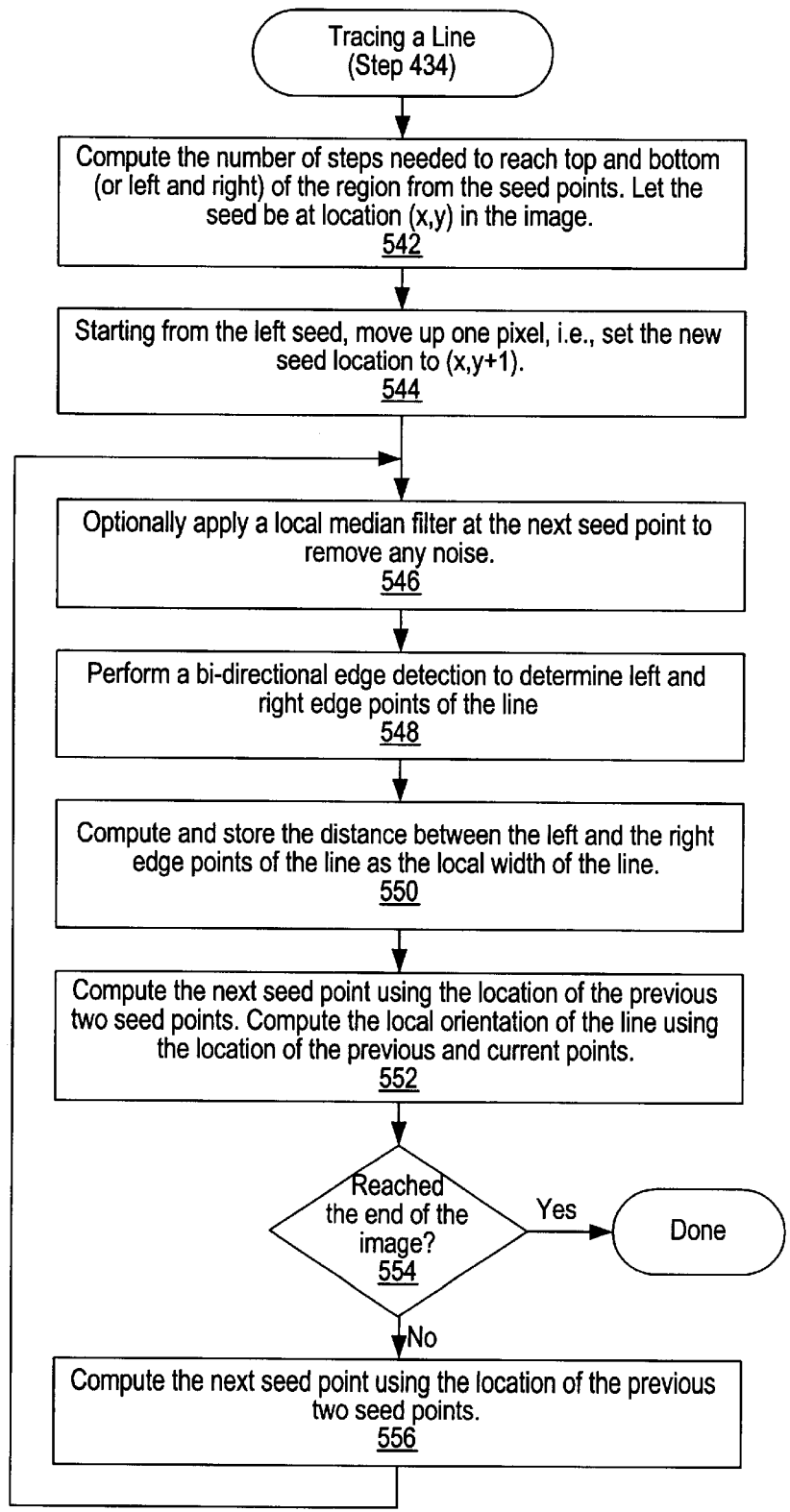
FIG. 6 is a flowchart diagram of a method for tracing and analyzing illumination lines performed in step 434 of FIG. 4.

FIG. 6—Illumination Line Tracing Method

FIG. 6 is a flowchart diagram illustrating operation of step 434 of FIG. 4 according to one embodiment, which comprises tracing illumination lines, preferably from each seed intersection point. The initial edge points found on the illumination line in step 432 are preferably used as seed (starting) points for tracing the left and right boundaries of the illumination line. Alternatively, where a training step was performed on the image, the seed (starting) points may be any predetermined point on the line, such as the bottom left edge point, the top left edge point, the bottom right edge point, or the top right edge point.

As shown, in step 542 the method may compute the number of steps (or pixels) needed to reach the top and bottom of the region (ROI) from the seed points (presuming the illumination lines are vertical in the image). Here the initial seed location may be referred to as location (x,y) in the image. Thus in step 542 the method may compute the number of pixels from the initial (x,y) seed location to the top of the ROI and the number of pixels from the initial (x,y) seed location to the bottom of the ROI. Where the illumination lines are horizontal, the ROI may be processed horizontally, and in step 542 the method may compute the number of steps (or pixels) needed to reach the left and right of the region (ROI) from the seed points.

In step 544, starting from the left seed point, the method moves up one pixel, e.g., sets the new seed location to (x, y+1). In other words in step 544 the method calculates a new pixel position that is one pixel up from the starting left seed point. If a prior training step was performed on an image, then the training step may have pre-computed coordinates along an edge of each illumination line. In this case, the method may not simply "move up one pixel", but rather may advance to the next pre-stored coordinate of the line along the respective edge of the line.

In step 546 the method may apply a local median filter at the new seed point to remove any noise. It is noted that other types of filters may be applied as desired, such as a spatial averaging filter or Gaussian filter. The filter may be applied to a plurality of pixels located in a neighborhood of the seed point or seed pixel. The filter may operate to remove noise from the image, such as dust particles or other foreign matter on the object which appear in the image of the object being analyzed. In one embodiment, the filter is a user selectable option, and thus the filter may only be applied in step 546 if requested by the user.

In step 548 the method may perform a bi-directional edge detection technique at the current location of the illumination line. The bi-directional edge detection technique is preferably performed along a path perpendicular to the current orientation of the line. The bi-directional edge detection technique operates to determine or identify the left and right edges of the illumination line at the current point along the illumination line. The technique performed in step 548 is described in greater detail with respect to the flowchart of FIG. 7.

In step 552 the method may compute and store the distance between the left and the right edge of the illumination line, wherein this distance is used as the local width of the illumination line.

In step 554 the method may compute the local orientation of the illumination line. The local orientation may be computed using the location of a previous and current edge point, e.g., the previous left edge point and the current left edge point.

In step 556 the method computes the next seed point using the location of the previous two seed points. Alternatively, as described above, the method may use a next pre-stored edge point that was pre-computed from a prior training step. Operation then returns to step 546, and steps 546–556 are repeated. If the seed location analyzed in the previous iteration is determined to be the last point in the illumination line in the direction being analyzed, then operation completes. Thus steps 546–554 are repeated a plurality of times. In other words, the process of finding illumination line boundary points is repeated until the top (or bottom) of the image (or ROI) is reached.

If the line tracing method of FIG. 6 began from the bottom (or top) of the illumination line, then a single pass from bottom to top (or top to bottom) may be performed. If the line tracing method of FIG. 6 began in the middle of the line from a seed line intersection, then after the top (or bottom) of the image (or ROI) is reached, the method starts from the original seed location and repeats the above process moving down (or up) the illumination line until the bottom (or top) of the image (or ROI) is reached. Thus, for example, the method described above is repeated, with the only difference being that the tracing is performed moving down (or up) the illumination line, rather than moving up (or down) the illumination line.

In some situations, two neighboring illumination lines may overlap due to excess widening or curvature of one or both of the neighboring lines. In one embodiment, the method is operable to continue tracking or tracing a illumination line even when the illumination line overlaps with a neighboring line for a certain distance. Thus the method is able to maintain a trace of the illumination line during the overlap and re-detect the edge when the overlap no longer occurs. This detection technique operates to perform an edge detection in a neighborhood along the edge using the last known orientation of the illumination line edge until the edge detection detects that the illumination line edge re-appears, and hence no longer overlaps with the neighboring line. The above method may then continue at the point where the illumination line edge reappears.

Figure 7:
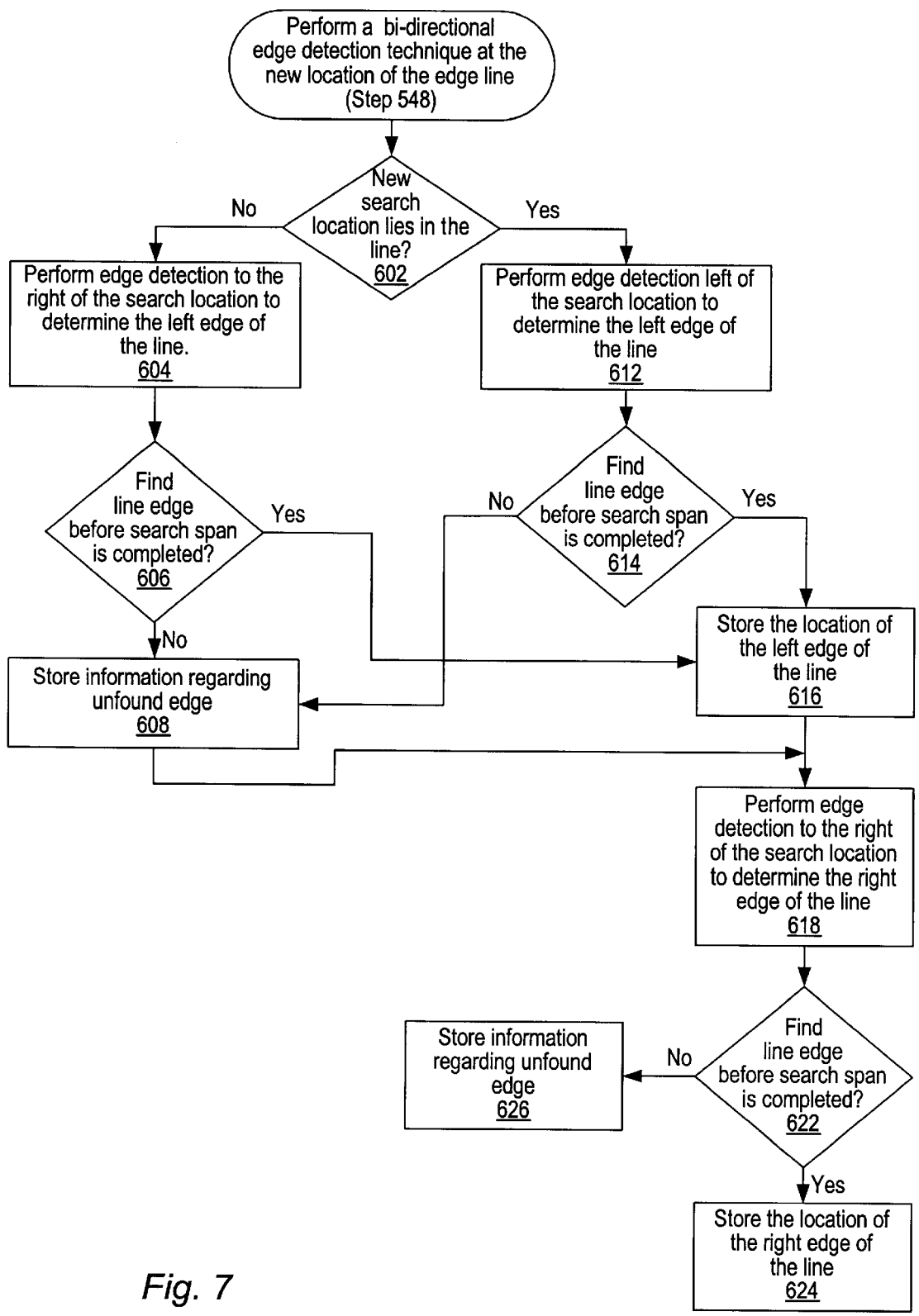
FIG. 7 is a flowchart diagram illustrating a bi-directional edge detection technique performed in step 548 of FIG. 6.

FIG. 7—Bi-Directional Edge Detection Technique

FIG. 7 is a flowchart diagram illustrating operation of step 548 of FIG. 6 according to one embodiment. The flowchart of FIG. 7 operates to first locate the left edge of the illumination line, followed by the right edge. However, the method may of course also first detect the right edge followed by the left edge.

In step 602 the method may determine if the new seed location lies inside the illumination line. This may be determined by the pixel value at this location, an edge detection method, or may be determined based on the previously computed width and orientation of the illumination line.

If the new seed location is determined to be inside the illumination line in 602, then in 604 the method moves left until it reaches the left edge on the illumination line. In other words, in 604 the method computes coordinates of pixels to the left of the new seed location and performs an edge detection until the last point on the illumination line (the left edge of the illumination line) is reached. The method may use a search span or scan region that is equal to or based on a prior determined width of the illumination line.

If the left line edge is found before the search span is completed as determined in 606, then operation proceeds to 616. If the search span completes and the left line edge has not been found as determined in 606, then in 608 information is stored regarding the unfound edge, and operation proceeds to 618.

If the new seed location is determined to lie outside the illumination line in 602 (to the left of the illumination line), then in 612 the method moves the seed location right until the first point on the left boundary of the illumination line is encountered. In other words, in 612 the method computes coordinates of pixels to the right of the new seed location and performs an edge detection until the first point on the left boundary of the illumination line is reached. The method may here also use a search span or scan region that is equal to or based on a prior determined width of the illumination line. The amount the method moves to the right may be predefined by the expected width, or previous computed width, of the illumination line (search span), e.g., equal to the previous width or 1.2× the previous width.

If the left line edge is found before the search span is completed as determined in 614, then operation proceeds to 616. If the search span completes and the left line edge has not been found as determined in 614, then in 608 information is stored regarding the unfound edge, and operation proceeds to 618.

In 616, once the left edge of the illumination line is determined, the location of the left edge of the illumination line is stored in memory. After the left edge of the illumination line is determined in 618, the method may begin at the left edge and search to the right for the right edge of the illumination line, e.g., by again using edge detection techniques. The search span used for this determination may be based on the expected width or previous computed width of the illumination line, e.g., 2× the line width. If a right illumination line edge is found before the scan is completed as determined in 622, this location value is stored as the right edge of the illumination line in 624. If the scan completes and a right illumination line edge has not been found as determined in 622, then in 626 information is stored regarding the unfound edge, and operation completes.

Thus, if no illumination line edges are found, or if only one edge is found, in the bi-directional edge detection, then the method may determine that a defect, e.g., a crack or dent, exists, and this information is recorded in the memory. The method may also detect two or more left edge points and/or two or more right edge points. If more than two edge points are detected for a left or right edge, then this may also indicate a defect or abnormality in the object being inspected, and this information is also recorded in the memory.

Determination of Defects

When the method has completed tracing the illumination line, e.g., both upward and downward, then the method has gathered information regarding the location of the illumination line, the width of the illumination line at each location (the local width), and the various local orientations of the illumination line at each location. After this tracing in step 434, as described above in step 436 the method may, if requested, compute curvature information of each respective illumination line.

The width information can then be used to detect abnormalities such as thinning or blooming (widening) in the illumination line. Very small cracks or dents may not break the illumination line but cause the illumination line to appear thinner or wider. The present method may be configured to indicate a defect, e.g., a crack, if the width at any point on a illumination line is less than the minimum width (a minimum width threshold may be input by the user, e.g., using a GUI) or is greater than a maximum width (a maximum width threshold may be input by the user, e.g., using a GUI.

The orientation or curvature information may be used to detect bends and/or folds in the illumination line. Cracks, dents, or other abnormalities may result in changes in orientation or increased curvature in the illumination line. The present method may be configured to indicate a defect if the curvature at any point on a illumination line is greater than a specified curvature threshold (a maximum curvature threshold may be input by the user, e.g., using a GUI).

Thus, information regarding thinning, bends and/or folds in the illumination line is useful in determining or detecting defects in the object.

In one embodiment, as noted above, the user may configure various parameters that are used in determining whether a defect should be identified. For example, the user may configure a thinning parameter or threshold which is used to determine whether a defect exists. If the amount of thinning exceeds the thinning threshold set by the user, then a defect may be identified. In addition, the user may configure a change in orientation parameter or curvature parameter which is also used to determine whether a defect exists. If the amount of change in orientation exceeds the threshold, then a defect may be identified.

These thresholds may be input through a graphical user interface of the software. For example, the thresholds may be input through a dialog box or other GUI element. In one embodiment, the user may view a sample image containing illumination lines and may graphically manipulate the width of the line or the curvature of the line, wherein this graphical manipulation operates to select the desired thresholds. In another embodiment, the user may view one or more sample images containing illumination lines that have various degrees of defects, and the user may select the image with the most defects that are still deemed acceptable or tolerable. Selection of the image may automatically result in the thresholds being generated from the minimum width and maximum curvature present in the selected image.

FIGS. 8A and 8B: Example ROIs

FIGS. 8A and 8B illustrate example images which include illumination line patterns superimposed on an object. FIGS. 8A and 8B also illustrate regions of interest (ROIs) that are configured on the images. Multiple ROIs can be defined on one image.

As shown, the user may configured one or more "Keep out" regions where line analysis is not desired to be performed. "Keep out" regions are useful to single out regions in the image that should not be analyzed for defects. For example, a region that corresponds to a portion of the object that by its nature would necessarily result in excess thinning or curvature of a line may be excluded using a "Keep out" region. In order to account for and exclude a "Keep out" region, the software program may programmatically define multiple regions of interests (ROI) in the image, wherein these multiple ROIs collectively operate to define the region desired to be analyzed and exclude the "Keep out" region(s). In one embodiment, these generated regions may be rectangular in shape. These multiple regions specify areas in the image that need to be analyzed for laser defects. Each of these regions may then be processed independently to identify laser defects. All the methods defined for processing an entire image can be applied to each region. Each illumination line is only traced within the region of interest.

Figure 9:
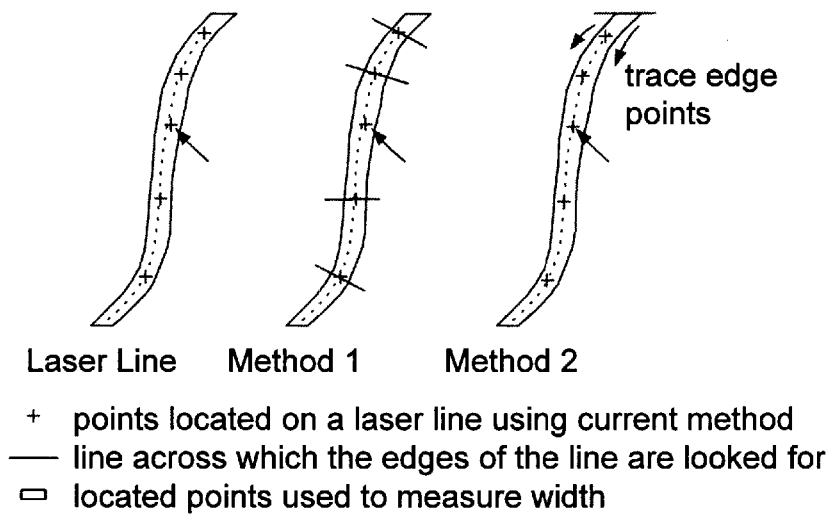
FIG. 9 illustrates various methods used in analyzing illumination lines, and particularly for detecting thinning of illumination lines.

FIG. 9—Tracing an Illumination Line

FIG. 9 illustrates an example illumination line as well as two different methods (labeled "Method 1" and "Method 2") that may be used to trace the edges of an illumination line.

As shown, the illumination line labeled "Method 1" illustrates the bi-directional edge detection technique described above with respect to FIGS. 6 and 7. At each detected point on the illumination line, this method performs a bi-directional edge detection technique along a path perpendicular to the current orientation of the line. The left edge and right edge are identified, as shown by the vertical lines displayed on the illumination line. These left and right edges can then be used in computing the local width of the line and the local orientation of the line. The local widths at each point along the illumination line can be used to detect thinning or widening in the illumination line, which may indicate a defect. The local orientations at each point along the illumination line can be used to detect abrupt changes in orientation of the illumination line, e.g., bends or folds, which may indicate a defect.

The illumination line labeled "Method 2" illustrates an alternate approach. In Method 2, the edge points of the illumination line are identified, and the method then tracks each of the edges independently. For example, this method may track or trace the left edge of the line, followed by tracking or tracing the right edge of the line. After each of the edges of the illumination line are independently tracked, this information can be used in computing the width of the illumination line and the orientation of the line, and hence can be used in identifying defects as described above.

Figure 10:
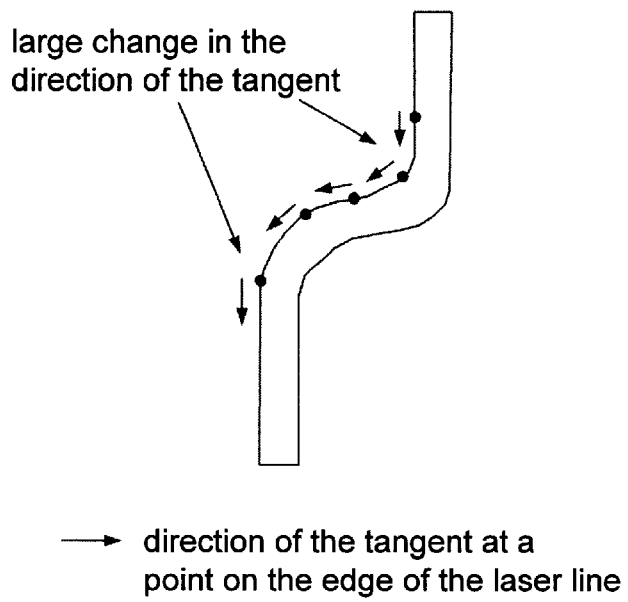
FIG. 10 illustrates a method for detecting change in curvature of a illumination line, which is useful in detecting bends and folds in the object being analyzed.

FIG. 10—Detection of Bends and Folds

FIG. 10 illustrates an example illumination line which includes a relatively large change in direction of the tangent at a point on the edge of the illumination line. In order to detect bends and folds, the line tracing algorithm finds the change in curvature at the edge points as it traverses along the line. Curvature may be defined as the rate of change of the angle tangent along the illumination line at the point of interest. If the rate of change exceeds the maximum rate of change for the appropriate region of interest, a bend or fold will be detected. As shown in FIG. 10, areas of bends or folds will be represented by large curvatures or large changes in orientation.

In one embodiment, the maximum rate of change is an input to the detection algorithm and can be set for each ROI in an image. This allows areas with expected bends to be inspected. Further, this allows areas in an image with expected bends to be inspected along with other areas of the image where a detected bend would indicate a defect.

Although the system and method of the present invention has been described in connection with several embodiments, it is not intended to be limited to the specific forms set forth herein, but on the contrary, it is intended to cover such alternatives, modifications, and equivalents, as can be reasonably included within the spirit and scope of the invention as defined by the appended claims.

What is claimed is:

1. A method for analyzing an image of an object to identify defects in the object, the method comprising:

projecting a pattern of lines on a surface of the object;

generating an image of the surface of the object, wherein the image includes the pattern of lines projected on the surface of the object, wherein each line includes a left edge and right edge;

for each respective line of a plurality of the lines, repeatedly determining left and right edge points of the respective line in the image, wherein said repeatedly determining operates to trace at least a portion of the respective line in the image;

determining whether a defect is present in the object using said left and right edge points of the plurality of the lines.

2. The method of claim 1, wherein said repeatedly determining comprises repeatedly determining left and right edge points of the respective line in the image using a bi-directional edge detection technique applied to a path perpendicular to the current orientation of the line.

3. The method of claim 1, further comprising:

determining a local width of the respective line for at least a subset of the left and right edge points of the respective line; and determining if a thinning of the respective line occurs which exceeds a threshold, wherein said determining if a thinning of the respective line occurs is based on one or more of the local widths of the respective line;

wherein a determined thinning of the respective line which exceeds the threshold indicates a possible defect in the object.

4. The method of claim 1, further comprising:

determining a local width of the respective line for at least a subset of the left and right edge points of the respective line; and determining if a blooming of the respective line occurs which exceeds a threshold, wherein said determining if a blooming of the respective line occurs is based on one or more of the local widths of the respective line;

wherein a determined blooming of the respective line which exceeds the threshold indicates a possible defect in the object.

5. The method of claim 1, further comprising:

determining a local orientation of the respective line for at least a subset of the left and right edge points of the respective line; and determining if a change in orientation of the respective line occurs which exceeds a threshold, wherein said determining if a change in orientation of the respective line occurs is based on one or more of the local orientations of the respective line;

wherein a determined change in orientation of the respective line which exceeds the threshold indicates a possible defect in the object.

6. The method of claim 1, wherein said repeatedly determining comprises:

repeatedly determining left and right edge points of the respective line in the image in an upward path from at least one point in the respective line;

repeatedly determining left and right edge points of the respective line in the image in a downward path from the at least one point.

7. The method of claim 1, further comprising applying a local filter to points in the line during said repeatedly determining.

8. The method of claim 1, wherein said repeatedly determining left and right edge points of the respective line in the image comprises:

at a first point in the image, determining if the first point lies within the respective line;

if the first point lies within the respective line, then performing an edge detection in a first direction away from the first point and parallel to an orientation of the respective line to determine a first edge of the respective line;

if the first point lies outside of the respective line, then performing an edge detection in a second direction away from the first point and parallel to an orientation of the respective line to determine a second edge of the respective line, wherein the second direction is opposite of the first direction.

9. The method of claim 1, wherein said repeatedly determining left and right edge points of the respective line in the image comprises:

at a first point in the image, determining if the first point lies within the respective line;

if the first point lies within the respective line, then:
performing an edge detection in a first direction away from the first point and parallel to an orientation of the respective line to determine a first edge of the respective line; and performing an edge detection in a second direction away from the first edge and parallel to an orientation of the respective line to determine a second edge of the respective line, wherein the second direction is opposite of the first direction;

if the first point lies outside of the respective line, then:

performing an edge detection in the second direction away from the first point and parallel to an orientation of the respective line to determine the second edge of the respective line; and performing an edge detection in the first direction away from the second edge and parallel to an orientation of the respective line to determine the first edge of the respective line.

10. The method of claim 1, wherein said repeatedly determining comprises:

determining if two or more lines overlap;

detecting when the two or more lines cease overlapping; and continuing said repeatedly determining after the two or more lines cease overlapping.

11. A method for tracing a line in an image, wherein the line is displayed on a surface of an object in the image, wherein the tracing is performed to identify defects in the object, wherein the line includes a left edge and a right edge, the method comprising:

projecting a pattern of lines on a surface of the object;

generating an image of the surface of the object, wherein the image includes the pattern of lines projected on the surface of the object, wherein each line includes a left edge and right edge;

a) determining left and right edge points of a line in the image;

b) determining a local width of the line for the left and right edge points of the line;

c) determining a local orientation of the first line for the left and right edge points of the line;

repeating (a)–(c) a plurality of times to substantially trace the line and determine information regarding the line;

determining whether a defect is present in the object using said local widths and said local orientations.

12. The method of claim 11, wherein said determining left and right edge points comprises determining left and right edge points of the line in the image using a bi-directional edge detection technique applied to a path perpendicular to the current orientation of the line.

13. The method of claim 11, wherein said determining whether a defect is present in the object using said local widths and said local orientations comprises determining if:

1) a thinning of the line occurs which exceeds a thinning threshold, wherein a determined thinning of the line which exceeds the thinning threshold indicates a possible defect in the object;

2) a blooming of the line occurs which exceeds a blooming threshold, wherein a determined blooming of the line which exceeds the blooming threshold indicates a possible defect in the object; and/or 3) a change in orientation of the line occurs which exceeds a change in orientation threshold, wherein a determined change in orientation of the line which exceeds the change in orientation threshold indicates a possible defect in the object.

14. The method of claim 11, further comprising applying a local filter to points in the line during said determining left and right edge points of the line.

15. The method of claim 11, further comprising:

determining if a thinning of the first line occurs based on one or more of the local widths of the first line;

determining if a change in orientation of the first line occurs based on one or more of the local orientations of the first line;

wherein a determined thinning of the first line indicates a possible defect in the object;

wherein a determined change in orientation of the first line indicates a possible defect in the object.

16. The method of claim 11, further comprising:

wherein (a)–(c) are repeatedly performed for each of at least a subset of the pattern of lines.

17. A method for analyzing an image of an object to identify defects in the object, the method comprising:

projecting a pattern of lines on a surface of the object;

generating an image of the surface of the object, wherein the image includes the pattern of lines projected on the surface of the object, wherein each line includes a left edge and right edge;

for each respective line of a plurality of the lines, tracking left and right edges of the respective line in the image;

determining whether a defect is present in the object using said left and right edge points of the plurality of the lines.

18. A method for tracing a line in an image, wherein the line is displayed on a surface of an object in the image, wherein the tracing is performed to identify defects in the object, wherein the line includes a left edge and a right edge, the method comprising:

projecting a pattern of lines on a surface of the object;

generating an image of the surface of the object, wherein the image includes the pattern of lines projected on the surface of the object, wherein each line includes a left edge and right edge;

a) tracking left and right edges of the line in the image;

b) determining a local width of the line for the left and right edge points of the line;

c) determining a local orientation of the first line for the left and right edge points of the line;

repeating steps (a)–(c) a plurality of times to substantially trace the line and determine information regarding the line;

determining whether a defect is present in the object using said local widths and said local orientations.

19. A memory medium comprising program instructions for tracing a line in an image, wherein the line is displayed on a surface of an object in the image, wherein the tracing is performed to identify defects in the object, wherein the line includes a left edge and a right edge, wherein the program instructions are executable to implement:

projecting a pattern of lines on a surface of the object;

generating an image of the surface of the object, wherein the image includes the pattern of lines projected on the surface of the object, wherein each line includes a left edge and right edge;

a) tracking left and right edges of the line in the image, wherein said tracking includes determining left and right edge points of the line;

b) determining a local width of the line from the left and right edge points of the line;

c) determining a local orientation of the first line for the left and right edge points of the line;

repeating steps (a)–(c) a plurality of times to substantially trace the line and determine information regarding the line;

determining whether a defect is present in the object using said local widths and said local orientations.

20. The method of claim 19, further comprising applying a local filter to points in the line during said tracking left and right edges of the line, wherein the local filter operates to remove noise from pixels being analyzed.

21. A machine vision system for analyzing an image of an object to identify defects in the object, the system comprising:

a light source configured to project a pattern of lines on a surface of the object;

a camera adapted to produce an image of the object, wherein the image includes the pattern of lines projected on the surface of the object, wherein each line includes a left edge and right edge;

a computer system coupled to the camera and adapted to receive the image of the object, wherein the computer system includes a memory medium and a processor, wherein the memory medium stores a line analysis software program, wherein, for each line of at least a subset of the pattern of lines, the processor is operable to execute the line analysis software program to:

a) determine left and right edge points of the line in the image;

b) determine a local width of the line from the left and right edge points of the line;

c) determine a local orientation of the first line for the left and right edge points of the line;

repeat (a)–(c) a plurality of times to substantially trace the line and determine information regarding the line; and determine whether a defect is present in the object using said local widths and said local orientations.

22. The machine vision system of claim 21, wherein the light source is configured to generate light;

wherein the machine vision system further comprises a pattern element positioned between the light source and the object, wherein the light source and the pattern element are configured to project the pattern of lines on the surface of the object.

23. The machine vision system of claim 21, wherein the processor is operable to execute the line analysis software program to apply a local filter to points in the line during said determining left and right edge points of the line, wherein the local filter operates to remove noise from pixels being analyzed.

24. A memory medium comprising program instructions for analyzing an image of an object to identify defects in the object, wherein a pattern of lines is operable to be projected on a surface of the object; and wherein an image of the surface of the object is operable to be generated, wherein the image includes the pattern of lines projected on the surface of the object, wherein each line includes a left edge and right edge;

wherein the program instructions are executable to implement:

for each respective line of a plurality of the lines, repeatedly determining left and right edge points of the respective line in the image, wherein said repeatedly determining operates to trace at least a portion of the respective line in the image;

determining a local width of the respective line for at least a subset of the left and right edge points of the respective line;

determining if at least one of a thinning or blooming of the respective line occurs which exceeds a threshold, wherein said determining if at least one of a thinning or blooming of the respective line occurs is based on one or more of the local widths of the respective line;

wherein at least one of a determined thinning or blooming of the respective line which exceeds the threshold indicates a possible defect in the object.

25. The memory medium of claim 24, wherein said repeatedly determining comprises repeatedly determining left and right edge points of the respective line in the image using a bi-directional edge detection technique applied to a path perpendicular to the current orientation of the line.

26. The method of claim 24, wherein the program instructions are executable to implement:

determining a local orientation of the respective line for at least a subset of the left and right edge points of the respective line; and determining if a change in orientation of the respective line occurs which exceeds a threshold, wherein said determining if a change in orientation of the respective line occurs is based on one or more of the local orientations of the respective line;

wherein a determined change in orientation of the respective line which exceeds the threshold indicates a possible defect in the object.

27. The memory medium of claim 24, wherein said repeatedly determining comprises:

repeatedly determining left and right edge points of the respective line in the image in an upward path from at least one point in the respective line;

repeatedly determining left and right edge points of the respective line in the image in a downward path from the at least one point.

28. The memory medium of claim 24, wherein the program instructions are executable to implement:

applying a local filter to points in the line during said repeatedly determining.

29. The memory medium of claim 24, wherein said repeatedly determining left and right edge points of the respective line in the image comprises:

at a first point in the image, determining if the first point lies within the respective line;

if the first point lies within the respective line, then performing an edge detection in a first direction away from the first point and parallel to an orientation of the respective line to determine a first edge of the respective line;

if the first point lies outside of the respective line, then performing an edge detection in a second direction away from the first point and parallel to an orientation of the respective line to determine a second edge of the respective line, wherein the second direction is opposite of the first direction.

30. The memory medium of claim 24, wherein said repeatedly determining left and right edge points of the respective line in the image comprises:

at a first point in the image, determining if the first point lies within the respective line;

if the first point lies within the respective line, then:
  performing an edge detection in a first direction away from the first point and parallel to an orientation of the respective line to determine a first edge of the respective line; and
  performing an edge detection in a second direction away from the first edge and parallel to an orientation of the respective line to determine a second edge of the respective line, wherein the second direction is opposite of the first direction;
if the first point lies outside of the respective line, then:
  performing an edge detection in the second direction away from the first point and parallel to an orientation of the respective line to determine the second edge of the respective line; and
  performing an edge detection in the first direction away from the second edge and parallel to an orientation of the respective line to determine the first edge of the respective line.

31. The memory medium of claim 24, wherein said repeatedly determining comprises:
  determining if two or more lines overlap;
  detecting when the two or more lines cease overlapping; and
  continuing said repeatedly determining after the two or more lines cease overlapping.

32. A method for analyzing an image of an object to identify defects in the object, the method comprising:
  projecting a pattern of lines on a surface of the object;
  generating an image of the surface of the object, wherein the image includes the pattern of lines projected on the surface of the object, wherein each line includes a left edge and right edge;
  for each respective line of a plurality of the lines, repeatedly determining left and right edge points of the respective line in the image, wherein said repeatedly determining operates to trace at least a portion of the respective line in the image;
  determining a local width of the respective line for at least a subset of the left and right edge points of the respective line; and
  determining if a thinning of the respective line occurs which exceeds a threshold, wherein said determining if a thinning of the respective line occurs is based on one or more of the local widths of the respective line;
  wherein a determined thinning of the respective line which exceeds the threshold indicates a possible defect in the object.

33. A method for analyzing an image of an object to identify defects in the object, the method comprising:
  projecting a pattern of lines on a surface of the object;
  generating an image of the surface of the object, wherein the image includes the pattern of lines projected on the surface of the object, wherein each line includes a left edge and right edge;
  for each respective line of a plurality of the lines, repeatedly determining left and right edge points of the respective line in the image, wherein said repeatedly determining operates to trace at least a portion of the respective line in the image;
  determining a local width of the respective line for at least a subset of the left and right edge points of the respective line; and
  determining if a blooming of the respective line occurs which exceeds a threshold, wherein said determining if a blooming of the respective line occurs is based on one or more of the local widths of the respective line;
  wherein a determined blooming of the respective line which exceeds the threshold indicates a possible defect in the object.

34. A method for analyzing an image of an object to identify defects in the object, the method comprising:
  projecting a pattern of lines on a surface of the object;
  generating an image of the surface of the object, wherein the image includes the pattern of lines projected on the surface of the object, wherein each line includes a left edge and right edge;
  for each respective line of a plurality of the lines, repeatedly determining left and right edge points of the respective line in the image, wherein said repeatedly determining operates to trace at least a portion of the respective line in the image, wherein said repeatedly determining comprises:
    repeatedly determining left and right edge points of the respective line in the image in an upward path from at least one point in the respective line;
    repeatedly determining left and right edge points of the respective line in the image in a downward path from the at least one point;
    determining whether a defect is present in the object using said left and right edge points of the plurality of the lines.

35. A method for analyzing an image of an object to identify defects in the object, the method comprising:
  projecting a pattern of lines on a surface of the object;
  generating an image of the surface of the object, wherein the image includes the pattern of lines projected on the surface of the object, wherein each line includes a left edge and right edge;
  for each respective line of a plurality of the lines, repeatedly determining left and right edge points of the respective line in the image, wherein said repeatedly determining operates to trace at least a portion of the respective line in the image, wherein said repeatedly determining left and right edge points of the respective line in the image comprises:
    at a first point in the image, determining if the first point lies within the respective line;
    if the first point lies within the respective line, then performing an edge detection in a first direction away from the first point and parallel to an orientation of the respective line to determine a first edge of the respective line;
    if the first point lies outside of the respective line, then performing an edge detection in a second direction away from the first point and parallel to an orientation of the respective line to determine a second edge of the respective line, wherein the second direction is opposite of the first direction; and
    determining whether a defect is present in the object using said left and right edge points of the plurality of the lines.

36. A method for analyzing an image of an object to identify defects in the object, the method comprising:
  projecting a pattern of lines on a surface of the object;
  generating an image of the surface of the object, wherein the image includes the pattern of lines projected on the surface of the object, wherein each line includes a left edge and right edge;
  for each respective line of a plurality of the lines, repeatedly determining left and right edge points of the respective line in the image, wherein said repeatedly determining operates to trace at least a portion of the respective line in the image, wherein said repeatedly determining left and right edge points of the respective line in the image comprises:

at a first point in the image, determining if the first point lies within the respective line;

if the first point lies within the respective line, then:
performing an edge detection in a first direction away from the first point and parallel to an orientation of the respective line to determine a first edge of the respective line; and
performing an edge detection in a second direction away from the first edge and parallel to an orientation of the respective line to determine a second edge of the respective line, wherein the second direction is opposite of the first direction;

if the first point lies outside of the respective line, then:
performing an edge detection in the second direction away from the first point and parallel to an orientation of the respective line to determine the second edge of the respective line; and
performing an edge detection in the first direction away from the second edge and parallel to an orientation of the respective line to determine the first edge of the respective line; and determining whether a defect is present in the object using said left and right edge points of the plurality of the lines.

37. A method for analyzing an image of an object to identify defects in the object, the method comprising:

projecting a pattern of lines on a surface of the object;

generating an image of the surface of the object, wherein the image includes the pattern of lines projected on the surface of the object, wherein each line includes a left edge and right edge;

for each respective line of a plurality of the lines, repeatedly determining left and right edge points of the respective line in the image, wherein said repeatedly determining operates to trace at least a portion of the respective line in the image, wherein said repeatedly determining comprises:
determining if two or more lines overlap;
detecting when the two or more lines cease overlapping; and
continuing said repeatedly determining after the two or more lines cease overlapping;

determining whether a defect is present in the object using said left and right edge points of the plurality of the lines.

* * * * *